United States Patent
Srinivasan et al.

(10) Patent No.: US 10,175,211 B2
(45) Date of Patent: Jan. 8, 2019

(54) CURRENT-EFFICIENT SUPPRESSOR AND PRETREATMENT DEVICE AND METHOD

(71) Applicant: DIONEX CORPORATION, Sunnyvale, CA (US)

(72) Inventors: Kannan Srinivasan, Tracy, CA (US); Rong Lin, Sunnyvale, CA (US); Christopher A. Pohl, Union City, CA (US); John Edward Madden, Sunnyvale, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 529 days.

(21) Appl. No.: 14/587,780

(22) Filed: Dec. 31, 2014

(65) Prior Publication Data

US 2016/0187305 A1    Jun. 30, 2016

(51) Int. Cl.
*G01N 30/96*    (2006.01)
*B01D 15/08*    (2006.01)
(Continued)

(52) U.S. Cl.
CPC .............. *G01N 30/48* (2013.01); *B01D 15/08* (2013.01); *B01D 15/36* (2013.01); *B01D 61/46* (2013.01);
(Continued)

(58) Field of Classification Search
CPC .......... G01N 1/40; G01N 1/405; G01N 30/06; G01N 30/14; G01N 30/48; G01N 30/96;
(Continued)

(56) References Cited

U.S. PATENT DOCUMENTS 3,618,589 A * 11/1971 Tavani .................... B01J 39/05
    127/36
4,242,097 A * 12/1980 Rich, Jr. .................. B01J 41/20
    210/198.2
(Continued)

FOREIGN PATENT DOCUMENTS

CN      1403811      3/2003
CN      1744945      3/2006
(Continued)

OTHER PUBLICATIONS

Dionex Column Product Manual for IonPac AS22 IonPac AS22-Fast, Doc No. 065119-08, Mar. 2013, 63 pages.
(Continued)

*Primary Examiner* — Joseph W Drodge

(57) ABSTRACT

An apparatus for treating an aqueous sample stream includes analyte ions. The apparatus comprises an ion exchange barrier; a sample stream flow channel; an ion receiving stream flow channel adjacent to the sample stream flow channel and separated therefrom by said first ion exchange bather. Stationary flow-through ion exchange packing is disposed in the sample flow channel of the same charge as the ion exchange bather. The ion exchange packing comprises a mixture of a first ion exchange portion with strong ionizable groups and a second ion exchange portion with weak ionizable groups of the same charge. First and second electrodes are in electrical communication with the sample stream flow channel and ion receiving flow channel.

19 Claims, 11 Drawing Sheets

(51) Int. Cl.

| | | |
|---|---|---|
| *B01D 15/36* | (2006.01) | |
| *B01D 61/46* | (2006.01) | |
| *B01D 61/52* | (2006.01) | |
| *B01J 39/26* | (2006.01) | |
| *B01J 41/20* | (2006.01) | |
| *B01J 47/04* | (2006.01) | |
| *B01J 20/281* | (2006.01) | |
| *G01N 30/00* | (2006.01) | |
| *G01N 30/02* | (2006.01) | |

(52) U.S. Cl.
CPC .............. *B01D 61/52* (2013.01); *B01J 39/26* (2013.01); *B01J 41/20* (2013.01); *B01J 47/04* (2013.01); *G01N 30/96* (2013.01); *G01N 2030/027* (2013.01); *G01N 2030/488* (2013.01); *G01N 2030/965* (2013.01)

(58) Field of Classification Search
CPC ..... G01N 2001/4038; G01N 2030/027; G01N 2030/143; G01N 2030/488; G01N 2030/965; B01D 15/08; B01D 15/12; B01D 15/36; B01D 15/361; B01D 15/362; B01D 15/363; B01D 15/367; B01D 17/06; B01D 61/44; B01D 61/445; B01D 61/46; B01D 61/48; B01D 61/485; B01D 61/52; B01D 2311/2603; B01J 39/06; B01J 39/07; B01J 39/26; B01J 41/05; B01J 41/07; B01J 41/20; B01J 47/04; B01J 47/026
USPC ...... 210/85, 198.2, 263, 269, 283, 284, 656, 210/659, 660, 663, 670, 677, 683, 685, 210/686; 204/520, 522, 523, 524, 533, 204/537, 542, 630–634, 672, 673; 422/70, 527; 436/161, 177
See application file for complete search history.

(56) References Cited

U.S. PATENT DOCUMENTS

| | | | |
|---|---|---|---|
| 4,265,634 A | 5/1981 | Pohl | |
| 4,290,775 A * | 9/1981 | Stevens | G01N 30/96 210/662 |
| 4,314,823 A * | 2/1982 | Rich, Jr. | G01N 30/08 210/198.2 |
| 4,474,664 A | 10/1984 | Stevens et al. | |
| 4,564,455 A * | 1/1986 | Flynn | B01J 49/18 210/675 |
| 4,751,189 A | 6/1988 | Rocklin | |
| 4,820,421 A * | 4/1989 | Auerswald | B01J 39/05 210/670 |
| 4,999,098 A | 3/1991 | Pohl et al. | |
| 5,045,204 A * | 9/1991 | Dasgupta | B01D 19/0031 204/257 |
| 5,248,246 A * | 9/1993 | Lew | F01C 1/063 417/420 |
| 5,248,426 A * | 9/1993 | Stillian | G01N 30/96 210/198.2 |
| 5,352,360 A | 10/1994 | Stillian et al. | |
| 5,423,965 A * | 6/1995 | Kunz | B01J 47/08 204/263 |
| 5,518,622 A | 5/1996 | Stillian et al. | |
| 5,569,365 A | 10/1996 | Rabin et al. | |
| 5,597,481 A | 1/1997 | Stillian et al. | |
| 5,597,734 A | 1/1997 | Small et al. | |
| 5,773,615 A | 6/1998 | Small et al. | |
| 5,788,826 A | 8/1998 | Nyberg | |
| 5,935,443 A * | 8/1999 | Anderson, Jr. | B01D 15/203 210/198.2 |
| 6,077,434 A * | 6/2000 | Srinivasan | G01N 30/96 204/520 |
| 6,325,976 B1 | 12/2001 | Small et al. | |
| 6,328,885 B1 | 12/2001 | Srinivasan et al. | |
| 6,331,250 B1 * | 12/2001 | Kaneko | B01D 15/1828 210/198.2 |
| 6,425,284 B1 | 7/2002 | Srinivasan et al. | |
| 6,436,719 B1 | 8/2002 | Srinivasan et al. | |
| 6,444,475 B1 | 9/2002 | Anderson, Jr. et al. | |
| 6,495,371 B2 | 12/2002 | Small et al. | |
| 6,508,985 B2 | 1/2003 | Small et al. | |
| 6,610,546 B1 | 8/2003 | Liu et al. | |
| 7,399,415 B2 | 7/2008 | Srinivasan et al. | |
| 7,473,354 B2 | 1/2009 | Liu et al. | |
| 7,517,696 B2 * | 4/2009 | Srinivasan | B01D 15/367 436/149 |
| 7,524,457 B2 | 4/2009 | Srinivasan et al. | |
| 8,216,515 B2 | 7/2012 | Liu et al. | |
| 8,333,891 B2 | 12/2012 | Wyatt | |
| 8,415,168 B2 | 4/2013 | Liu et al. | |
| 2005/0034997 A1 | 2/2005 | DiMascio et al. | |
| 2005/0258360 A1 | 11/2005 | Whitehouse et al. | |
| 2006/0057733 A1 | 3/2006 | Liu et al. | |
| 2006/0186046 A1 | 8/2006 | Liu et al. | |
| 2006/0254969 A1 | 11/2006 | Yamanaka et al. | |
| 2007/0051684 A1 * | 3/2007 | Grebenyuk | B01D 61/48 210/681 |
| 2007/0062873 A1 | 3/2007 | Liu et al. | |
| 2008/0053830 A1 * | 3/2008 | Tsonev | B03C 5/00 204/661 |
| 2008/0203029 A1 * | 8/2008 | Deorkar | B01J 20/285 210/659 |
| 2008/0314750 A1 * | 12/2008 | Hagner-McWhirter | B01D 15/168 204/459 |
| 2009/0127200 A1 | 5/2009 | Dasgupta et al. | |
| 2009/0166293 A1 | 7/2009 | Srinivasan et al. | |
| 2009/0308757 A1 | 12/2009 | Crettenand | |
| 2013/0306565 A1 | 11/2013 | Davis | |
| 2014/0134050 A1 | 5/2014 | Srinivasan et al. | |
| 2014/0332387 A1 | 11/2014 | Srinivasan et al. | |

FOREIGN PATENT DOCUMENTS

| | | |
|---|---|---|
| CN | 101952717 A | 1/2011 |
| CN | 103969378 A | 8/2014 |
| EP | 0032770 B1 | 6/1984 |
| EP | 0180321 B1 | 2/1991 |
| EP | 0442224 A2 | 8/1991 |
| EP | 0555962 A2 | 8/1993 |
| EP | 2390660 A1 | 11/2011 |
| JP | 2013195301 | 9/2013 |
| WO | 2004070377 A2 | 8/2004 |
| WO | WO2006034182 A1 | 3/2006 |
| WO | 2008024500 A2 | 2/2008 |
| WO | WO2012074455 A1 | 6/2012 |

OTHER PUBLICATIONS

Dionex Column Product Manual for IonPac AS23, Doc No. 065120-06, May 2013, 51 pages.
Dionex Column Product Manual IonPac AS15, Document No. 031362-10, Jun. 2014, 60 pages.
Dionex Product Manual ASRS(R) 300 CSRS(R) 300, Document No. 031956, Rev, 05, Aug. 2007, 51 pages.
Dionex Product Manual for ERS 500 Suppressor, Doc No. 031956-09, Nov. 2013, 69 pages.
Dionex Product Manual for IonPac(R) CG12A IonPac(R) CS12A, Doc No. 031132, Rev. 09, May 2010, 78 pages.
Dionex Product Manual IonPac AS18 Fast, Document No. 031878-08, Jun. 2012, 54 pages.
Douglas et al., "New suppressor technology improve trace level anion analysis with carbonate-hydrogencarbonate mobile phases," J Chrom A, 956, 2002, 47-51.
Saari-Nordhaus et al., "Recent advances in ion chromatography suppressor improve anion separation and detection," J Chrom A, 956 (2002) 15-22.

(56) References Cited

OTHER PUBLICATIONS

Srinivasan et a., "Suppressor Design and Detection for Ion Chromatography" in: "Applications of Ion Chromatography for Pharmaceutical and Biological Products," Mar. 9, 2012, John Wiley & Sons, Inc., pp. 91-105.
U.S. Appl. No. 13/674,738, filed Nov. 12, 2012, to Srinivasan (specification, claims, abstract only).

* cited by examiner

CURRENT-EFFICIENT SUPPRESSOR AND PRETREATMENT DEVICE AND METHOD

BACKGROUND OF THE INVENTION

The present application relates to a current efficient electrolytic device and method for reducing the concentration of matrix ions of opposite charge to ions to be analyzed, and specifically for use in an ion chromatography suppressor or to a pretreatment device.

SUMMARY

According to the invention, an apparatus is provided for treating an aqueous sample stream including analyte ions. The apparatus comprises a first ion exchange barrier capable of passing only ions of opposite charge to the analyte ions; a sample stream flow channel, an ion receiving stream flow channel adjacent to the sample stream flow channel and separated therefrom by the first ion exchange barrier, stationary flow-through first ion exchange packing disposed in the sample stream flow channel of the same charge, as the first ion exchange barrier. The stationary flow-through first ion exchange packing with exchangeable ions of opposite charge to the analyte ions comprises a mixture of a first ion exchange portion with strong ionizable groups and a second ion exchange portion with weak ionizable groups, both portions having ionizable groups of the same charge, positive or negative. Also, it includes first and second electrodes in electrical communication with the sample stream flow channel and the ion receiving stream flow channel, respectively. Also, a method is provided for using the apparatus.

DETAILED DESCRIPTION OF EMBODIMENTS

Figure 1:
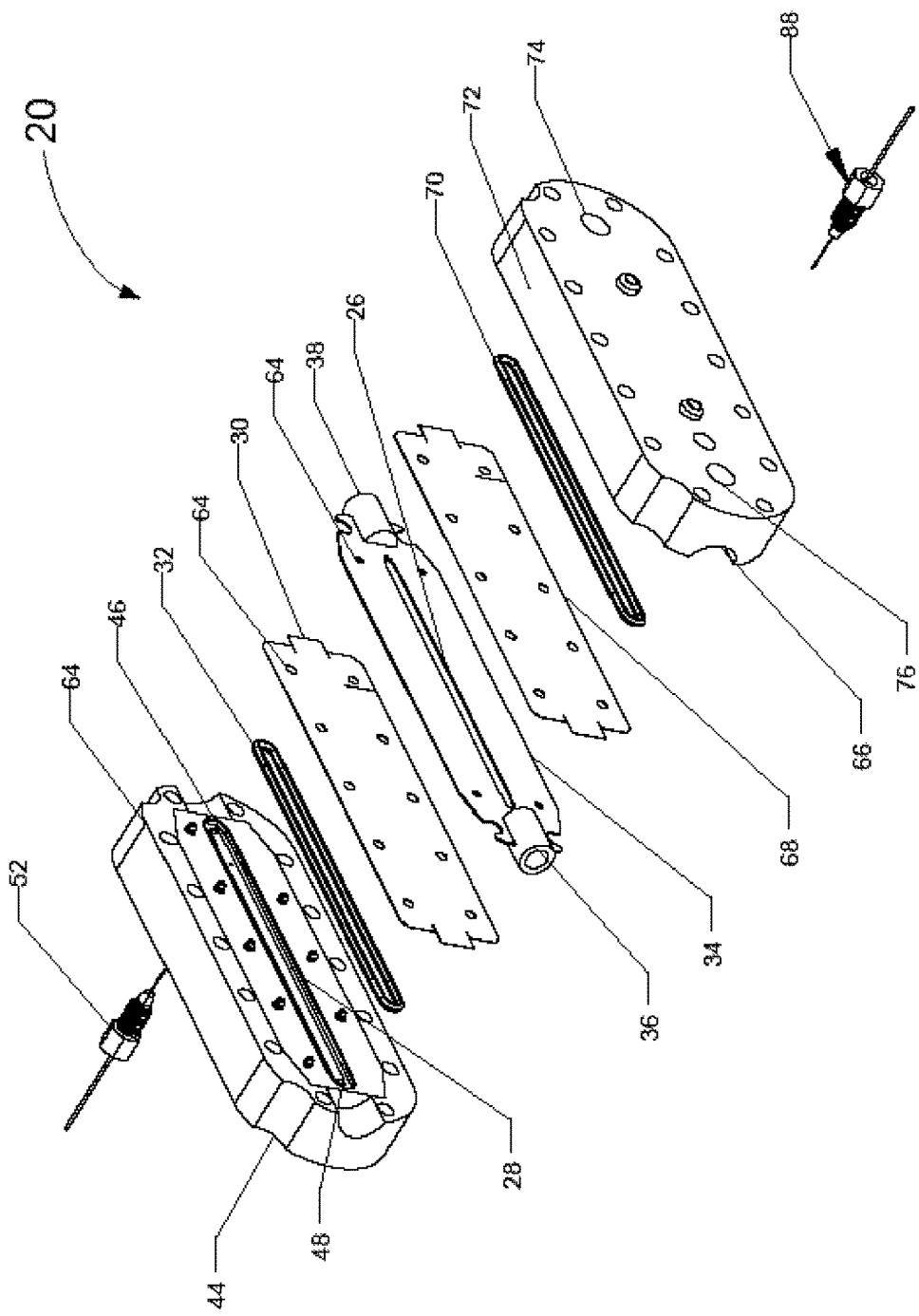
FIG. 1 illustrates an exploded perspective view of a suppressor for use in the present invention.

The suppressor or pretreatment device and method of the present invention are improvements over that of issued U.S. Pat. No. 6,077,434 (hereinafter the '434 patent), and of the ones described in US 2014/0134050 A1 (hereinafter the '050 publication). In general, the invention uses the apparatus and method of the '434 patent except where otherwise described herein. The most significant difference relates to the packing in the sample stream flow channel. Thus, the description of the suppressor and pretreatment device, and definitions set forth in the '434 patent, at column 4, line 11 through column 12, line 44, particularly, FIG. 1-FIG. 8 and the accompanying description, are incorporated at this point by reference. The pretreatment device and method of U.S. Pat. No. 5,597,481 are also incorporated by reference.

Electrolytic suppressors such as disclosed in the '434 patent are in widespread use in the field of ion chromatography as they confer significant ease of use to the user and, in the recycle mode, do not require any additional reagents for operation. In operation the user inputs a current for a given eluent concentration. The current needed to suppress a given eluent at 100% current efficiency can be easily calculated based on Faraday's equation.

$$i_{100} = \frac{fcv}{60} \quad (1)$$

where
  $i_{100}$ is the current in mA for a device with 100% current efficiency
  f is Faraday's constant
  c is the concentration in M
  v is the flow rate in mL/min By way of example, for suppressing an eluent comprising of 20 mM potassium hydroxide eluent the above equation calculates the required current to be approximately 32 mA. As the current efficiency of a suppressor device decreases the current required for suppression increases. It is known that if the current applied increases for a given suppressor the noise increases and the wattage increases. Maintaining a high current efficiency is therefore important as this ensures that the suppressor draws the current required for suppression.

It has been discovered that the use of current efficient devices for constant voltage operation as disclosed in the '434 patent has a limitation in that knowledge of the optimal voltage setting is needed for proper chromatographic operation. When the set voltage deviates from the optimum voltage, the net effect is loss of peak efficiency and peak asymmetry. Such devices preferably operate only at the predetermined optimum voltage and the optimum voltage can only be obtained from experimentation by running the experiment under a variety of voltages and decipher the optimum voltage. This approach is cumbersome and adds significant time to the method development aspect. Further suppressor to suppressor variation and system to system variation is expected to make the method less reliable. The present invention solves these issues.

The device of the present invention is less sensitive to applied voltage variations with peak efficiency and peak shapes preserved compared to the '434 patent. The suppressor performs reliably under a variety of eluent and system conditions. Constant current operation is feasible according to the present invention. The end user can provide input on the applied current. For example, when using an electrolytic eluent generation, the eluent strength is known and this input can be used to calculate the applied current required for the suppressor of the present invention. In an embodiment, the substantially constant voltage may vary by +/−10%, +/−5%, +/−4%, +/−3%, +/−2%, +/−1%, +/−0.1%, or less than the absolute value of +/−0.1% of the set voltage.

One embodiment of the present invention, based on the suppressor described in the '434 patent, is a single ion exchange barrier (preferably an ion exchange membrane) suppressor-type device. The present description generally will use the terms "ion exchange membrane" and "ion exchange barrier" interchangeably. The apparatus can be used for ion chromatographic or pretreatment of a liquid sample stream including analyte ions as described in the '434 patent. According to the invention, apparatus is provided for treating an aqueous sample stream including analyte ions. The apparatus comprises (a) an ion exchange barrier capable of passing only ions of opposite charge to the analyte ions; (b) a sample stream flow channel, (c) an ion receiving stream flow channel adjacent to the sample stream flow channel and separated therefrom by the first ion exchange barrier, and (d) stationary flow-through first ion exchange packing disposed in the sample flow channel of the same charge as the first ion exchange barrier. The packing has exchangeable ions of opposite charge to the analyte ions and comprises a mixture of a first ion exchange portion with strong ionizable groups and a second ion exchange portion with weak ionizable groups, both portions having ionizable groups of the same charge, positive or negative. Also, it includes first and second electrodes in electrical communication with the sample stream flow channel and the ion receiving flow channel, respectively. Also, a method for using the apparatus is also provided.

In a preferred embodiment, the sample stream flow channel ion exchange packing comprises a bed of ion exchange particles comprising the first and second ion exchange portions. The ion exchange particles in the sample stream flow channel can also be referred to as a stationary flow-through first ion exchange packing.

The least expensive way to make such an ion exchange bed is to pre-mix ion exchange particles (e.g., ion exchange resin) in an intimate mixture and then to pack the mixed particle bed into the sample stream flow channel. It is possible to provide a mixture of strong and weak ionizable groups (ion exchange functionalities) in the packing via chemical synthesis or grafting approaches and comprising an ion exchange screen or an ion exchange monolith, but it would be far more expensive and complicated to do so. The present description will refer to the preferred mixed ion exchange particle bed.

As used herein, the terms "strong ionizable groups" and "weak ionizable groups" are defined to have the same meaning as ascribed to them by one of ordinary skill in the chromatography field. Typically, the strong ionizable groups for a cation exchanger are strong acids and for an anion exchanger are strong bases. Typically, the weak ionizable groups for a cation exchanger are weak acids and for an anion exchanger are weak bases. The first ion exchange portion typically comprises at least 40%, 50%, 60%, 65%, 70%, 75%, 80%, 85%, 90%, 95%, or 97% by weight of the mixture. The second ion exchange portion typically comprises at least 3% and less than 60%, 55%, 50%, 45%, 40%, 35%, 30%, 25%, 20%, 15%, 10%, or 5% by weight of the mixture. Suitable strong ionizable groups are known in the chromatography field. Dowex 50WX8 and Amberlite IR 122 are commonly used strong acid cation exchange resins. For use as a cation exchanger, they include ion exchange particles in the sulfonated, methylsulfonated, or sulfopropyl form, preferably in the sulfonated form. Chelex-100 and Bio-Rex 70, and Amberlite IRC-76 resins are commonly used weak acid cation exchange resins. For cation exchange, suitable weak ionizable groups are in the carboxylated, chlorocarboxylate, or phosphonate form, preferably in the carboxylated form.

For use as an anion exchanger, suitable strong and weak ionizable groups are also known. Strong ionizable groups include quarternary amines which could be preferably be trialkyl amine based or dialkyl 2-hydroxy ethyl ammonium based. AG 1-X8 and AG 2-X8 are example of this type of resins from Biorad laboratories. Weak ionizable groups are tertiary amine-based or secondary amine based groups. AG 3-X4 and AG 4-X4 are 4% crosslinked resin with a tertiary amine functional group from Biorad Laboratories. Diethylaminoethyl is an example of a weak base ionizable group. More information can be found at http://www.bio-rad.com/en-us/category/analytical-grade-ion-exchange-resins.

In a preferred embodiment, the ion receiving flow channel is packed with strong ionizable groups ion exchange medium, such as of the type described in the '434 patent. Such packing has the same charge as its adjacent ion exchange membrane and preferably is an ion exchange screen but can be other packing such as a packed bed of ion exchange particles or an ion exchange monolith.

Also, the invention is applicable to a sandwich-type suppressor device of the type described in the '434 patent with a second ion exchange membrane between the sample stream flow channel and an ion source flow channel, and packing in the ion source flow channel of the same charge and type used in the ion receiving flow channel.

A more recent suppressor device is described in the '050 publication. FIG. 1 herein is FIG. 2 of that publication. Referring now to FIG. 1, there is depicted an exploded exemplary suppressor 20 for the present invention including a primary or eluent channel 26 (e.g., sample stream flow channel), a first regenerant channel 28 (e.g., ion receiving flow channel), a first charged barrier 30 (e.g., first ion exchange barrier) and a first sealing member 32. Unlike the suppressor of the '434 patent, where eluent and regenerant channels are defined and sealed by gasketed screens, the eluent channel 26 of FIG. 1 is formed in a first eluent channel member 34 and the first regenerant channel 28 is formed on a first block 44 that is typically disposed on a side of the eluent channel member 34. The first charged barrier 30 is disposed between the eluent channel member 34 and the first block 44 and separates the eluent channel 26 from the first regenerant channel 28. The first sealing member 32 can be disposed against the first charged barrier 30 for sealing one of the eluent channel member 34 and the first regenerant channel 28. As illustrated in FIG. 1, the first sealing member 32 directly forms the seal to the first regenerant channel 28 and indirectly forms the seal to the eluent channel 26 by urging the first charged barrier 30 against the eluent channel member 34. The first sealing member 32 is disposed between the first charged barrier 30 and the first block 44. The first sealing member 32 partially defines the first regenerant channel 28 and provides a liquid-tight seal to the eluent channel 26 and the first regenerant channel 28. One will appreciate that in various embodiments, the suppressor may be configured with a sealing member utilized to form an eluent channel between the charged barrier and the eluent channel plate, and a regenerant channel defined by the compartment in the first block and enclosed with the other side of the first charged barrier. The function of the sealing member is to seal between the eluent channel member and the first block via the first charged barrier.

Referring back to FIG. 1, electrical connectors 52 and 88 may be used to facilitate electrical communication between the electrodes. The first regenerant channel 28 has a regenerant inlet 46 at one end and a regenerant outlet 48 at the other end of the first regenerant channel 28. A second regenerant channel 66, a second charged barrier 68 and a second sealing member 70, which may be formed in a similar or substantially the same way as the first regenerant channel 28, the first charged barrier 30 and the first sealing member 32. The eluent channel member 34, the first charged barrier 30, and the first block 44, each of them may include alignment features 64 in the form of a plurality of holes for facilitating alignment of these components. The eluent inlet 36 and outlet 38 are formed independently in the separated eluent channel member 34. The second regenerant channel 66 may be formed on a second block 72 that is typically disposed on the other side of the eluent channel member 34 opposite to the first block 44. The second regenerant channel 66 has a regenerant inlet 74 at one end, which may be in fluidic communication with a regenerant reservoir or back pressure coils, and a regenerant outlet 76 at the other end, which may be in fluid communication with waste, eluent generator or other devices.

The invention is further applicable to a capillary suppressor-type device such as described in U.S. Pat. Nos. 8,415,168 and 8,216,515, using the packing of the present invention in the sample stream flow channel.

In the present invention, a mixed ion exchange medium having strong ionizable ions and weak ionizable ions improves the current efficiency of the device. The following is a theoretical discussion of an anion analysis system including the weak ionizable group carboxylate form and the strong ionizable group sulfonate form of the resin particle, e.g. mixture packed in the sample stream flow channel of an anion suppressor as per the present invention. For anion analysis, a carboxylate form resin in the hydronium form is sufficiently resistive in the hydronium form to prevent easy transport of hydronium ions. The carboxylate form of the resin in hydronium form is a neutral form of the carboxylic acid molecule, and therefore is not electrically conductive and inhibits transport of hydronium ion across the resin in an electric field. In contrast to the hydronium form with the dissociated cation form such as the sodium form transport of the sodium ion is relatively facile in the carboxylate form resin.

Because the sulfonated form of the resin is strongly ionized, the transport of the ions in an electric field is independent of the form of the resin and both hydronium and the sodium form are transported freely. Since hydronium ion has a five fold higher electrical mobility than sodium ion, a fully ionized resin is extremely conductive in the hydronium ion form. This leads to poor current efficiency, particularly in the sample stream channels of the prior art which are packed entirely with the sulfonated form of the resin. Similarly packing the sample stream flow channels with the carboxylate form of the resin alone will inhibit transport of the hydronium at the outlet. Although this effect may lead to improved current efficiency due to poor current carrying ability in the outlet zone of the sample stream flow channel, the analyte peaks generally are distorted in this zone. Further, since the carboxylate form of the resin is highly resistive the voltage requirements of the device to generate the required current for suppression become prohibitive. In other words, the device has high electrical resistance.

By mixing the weak ionizable group (carboxylate) particles (e.g., ion exchange resin particles) with the strong ionizable group (e.g., sulfonated) ion exchange resin particles as per the present invention both resistive and conductive regions are created within the sample stream flow channel. As per the present invention the resistive zones preserve the current efficiency of the device by slowing down the transport of hydronium ions. By slowing the hydronium ion, the overall transport of hydronium is inhibited which is believed to achieve current efficiency in the suppressor of the present invention. Further, since there are conductive sections in the sample stream flow channel, analyte peaks after suppression are not distorted. Another benefit is the relatively low voltage required for the device operation during suppression since there is a conductive section in the outlet of the device.

Thus the benefit of having strong ionizable group (e.g., strong acid sulfonated) form resin is the relatively high conductivity which allows for some transport of ions particularly when the voltage is far from optimal. Under these conditions there is minimal or no net distortion of the analyte zones and excellent peak shapes are achieved by the device of the present invention.

The current efficient devices of the present invention produce improved current efficiency performance and peak shape performance.

According to the present invention it is not necessary to operate close to an optimum voltage. However, the device of the present invention could be calibrated by determining a voltage that would facilitate suppression of a maximum eluent concentration. For example, for anion analysis with eluent generation systems the device voltage would be determined that would facilitate the suppression of 100 mM KOH. Now this voltage would be sufficient to suppress any concentration between 0 and 100 mM KOH. Thus by predetermining the voltage to suppress the maximum concentration the device to device variation is minimized and there is no need to pursue any other experimentation.

The device of the present invention has at least the following advantages over the prior art suppressor devices such as disclosed in the '434 patent:

a) Current efficiency is achieved in the devices of the present invention by mixing fully ionized materials with partially ionized materials. Operation at a current efficient regime has benefits of low wattage and lower leachate levels that translate into a low noise performance. With gradients, the device self-adjusts to the influent concentration and is able to provide noise free operation.

b) The device is less sensitive to voltage changes and peak shape and efficiencies are preserved. in contrast the suppressors of the prior art operate at a relatively narrow regime and do not provide the flexibility required for analysis. The insensitivity to the applied voltage is feasible due to the conductive pathways in the present invention.

c) The device can operate with one applied voltage thereby conferring ease of use to the user. Since the device is not sensitive to the applied voltage application, one voltage for a given application is feasible. In contrast, optimization typically is needed for the current efficient devices of the prior art since the peak shape is non optimal as one deviates further from the current efficient voltage. The reason for this stems from not having sufficient current carrying ability in the prior art devices. In contrast due to the combination of fully functionalized (with strong ionizable groups) ion exchange particles and weakly dissociated (weak ionizable groups) ion exchange particles, there is a pathway for current to be transported in the present design which preserves the peak shapes.

d) Constant current conditions also are feasible in the devices of the present invention. The device has conductive elements in the design that allows for transport of excess current if required. In suppressors of the prior art that are current inefficient, such transport would result in poor performance. In current efficient devices of the prior art operation under constant current is feasible if the current is fine tuned to the influent equivalents of the eluent. This approach however is cumbersome. In contrast due to the conductive elements in the present design the devices of the present invention are more resilient to current changes.

As set forth above, the apparatus and method of the present invention is applicable to the following types of systems disclosed in the '434 patent:

(1) Use in combination with apparatus for performing ion chromatography. The apparatus further comprises a chromatographic separator in fluid combination with the sample stream flow channel; and a detector for the analyte ions in fluid communication with the outlet of the sample stream flow channel, (2) Use of the apparatus for pretreatment of a sample stream and in combination with chromatography apparatus. The apparatus further comprises a chromatographic separator having an inlet and an outlet. The chromatographic separator inlet is in fluid communication with the sample stream flow channel. A detector is provided for the analyte in fluid communication with the outlet of the chromatographic separator, (3) The apparatus further comprising a second ion exchange barrier on the opposite side of the sample stream flow channel from the ion exchange barrier and of the same charge, positive or negative. An ion source channel is provided adjacent the second ion exchange barrier.

(4) A method comprising flowing the sample stream through the sample stream flow channel and out an outlet thereof; and simultaneously flowing an aqueous ion receiving stream through the ion receiving flow channel separated therefrom by an ion exchange barrier capable of passing only ions of opposite charge to the analyte ions, while passing a current between the sample stream flow channel and the ion receiving flow channel. The same packing described above is disposed in the sample stream flow channel of the same charge as the ion exchange barrier, and In order to illustrate the present invention, the following non-limiting examples of its practice are provided.

COMPARATIVE PRIOR ART EXAMPLE 1 (ANION ANALYSIS)

Figure 2:
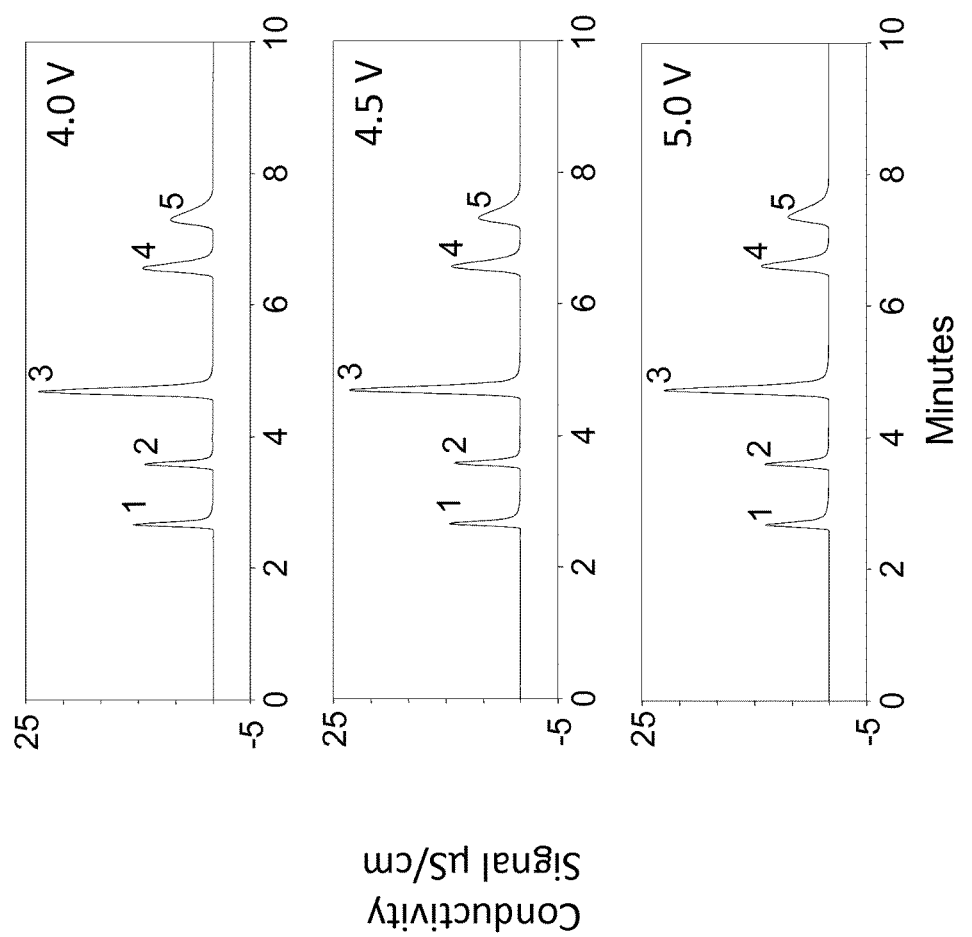
FIG. 2 is a chromatogram illustrating the performance of a prior art suppressor.

A 2 mm Thermo Scientific™ ASRS™ suppressor sold by Thermo Fisher Scientific was fitted with a neutral screen as described in the '434 patent. The device was nearly 100% current efficient. The device was used as a suppressor by applying various constant voltages across the device. A prototype IonPac™ AS18 column 2×250 mm was used in this work with a 32 mM KOH eluent. The flow rate was 0.25 ml/min and the injection loop size was 5 µL. A sample comprising of five standard anions such as fluoride (peak 1, 2 mg/L), chloride (peak 2, 3 mg/L), sulfate (peak 3, 15 mg/L), nitrate (peak 4, 10 mg/L) and phosphate (peak 5, 15 mg/L) was analyzed. The suppressor was operated with a DC power supply under constant voltage conditions of 3.5 volt, 4.0 volt and 4.5 volt. The resulting chromatograms are shown in FIG. 2. The results indicated significant loss of peak efficiency and peak shape issues as the voltage increased. A summary of the results are presented in Tables 1 and 2 below.

TABLE 1

Effect of applied voltage on peak efficiency

| Applied Voltage | $F^-$ | $Cl^-$ | $SO_4^{2-}$ | $NO_3^-$ | $PO_4^{3-}$ |
|---|---|---|---|---|---|
| 4.0 V | 7322 | 10773 | 8593 | 10354 | 5753 |
| 4.5 V | 6307 | 10263 | 8416 | 10171 | 5738 |
| 5.0 V | 5523 | 9956 | 8192 | 9873 | 5682 |

The early elutor fluoride is significantly impacted by the applied voltage and the efficiency drop from 4.0 to 5.0 volt is about 25%. Chloride also showed a 8% decline.

TABLE 2

Effect of applied voltage on peak asymmetry

| Applied voltage | $F^-$ | $Cl^-$ | $SO_4^{2-}$ | $NO_3^-$ | $PO_4^{3-}$ |
|---|---|---|---|---|---|
| 4.0 V | 1.62 | 1.27 | 1.32 | 1.42 | 1.81 |
| 4.5 V | 1.76 | 1.31 | 1.32 | 1.43 | 1.90 |
| 5.0 V | 1.90 | 1.36 | 1.36 | 1.44 | 1.91 |

The peak asymmetry showed an increasing trend with voltage suggesting that the peak shape was getting worse with the increasing applied voltage using a current efficient device. The outlet portion of this prior art suppressor device does not have sufficient current carrying ability and the peak shapes are therefore affected in this zone when the voltage is increased.

EXAMPLE 2 (ANION ANALYSIS)

A Thermo Scientific™ AERS 2 mm suppressor of the present invention was assembled (available from Thermo Fisher Scientific) as generally described in the U.S. Pre-Grant Publication 2014/0134050A1. However, in this device, the eluent channel of the device was packed with cation exchange resin with a composition comprising of 90% by weight of a sulfonated cation exchange resin and 10% of a weak carboxylated cation exchange resin. The device was tested using AS 18 chemistry under similar conditions as to Example 1.

Figure 3:
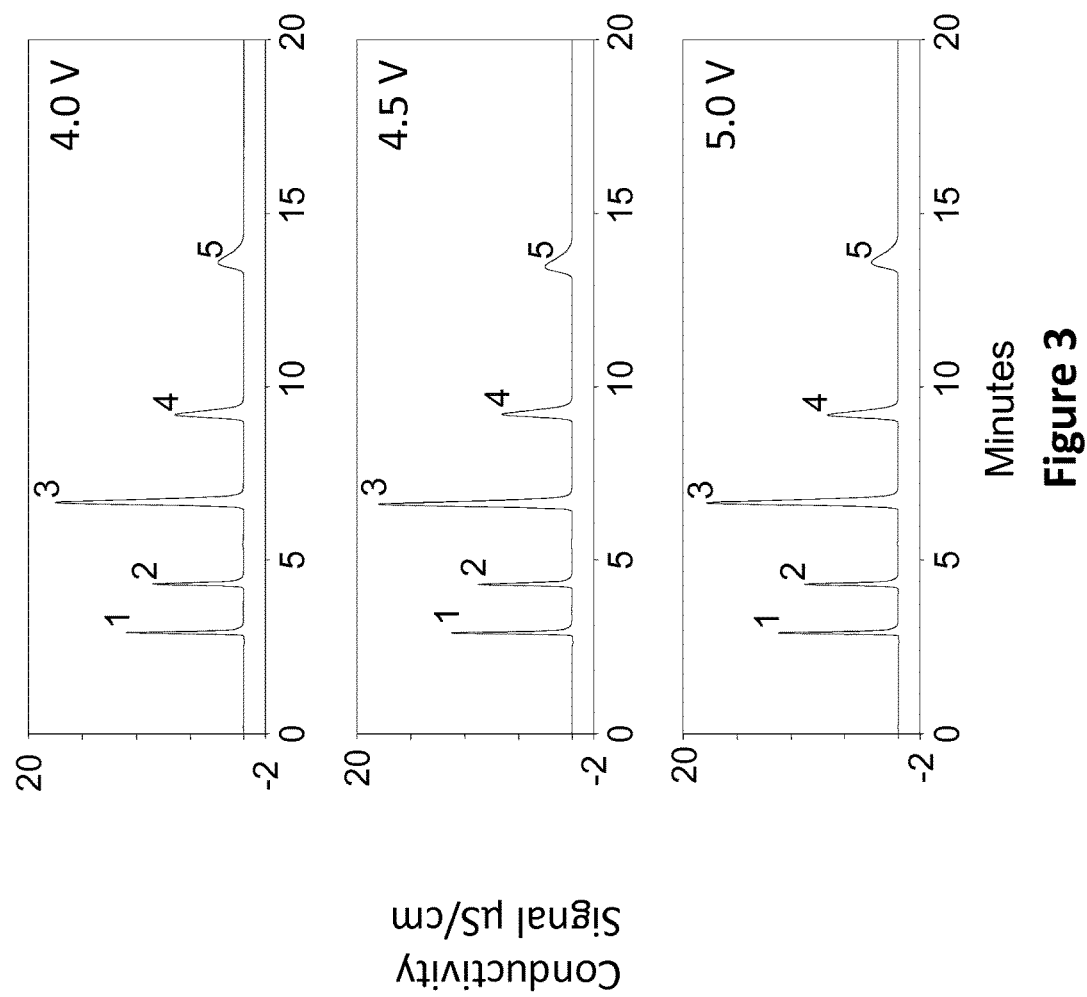
FIG. 3 is a chromatogram illustrating the present invention.

The results shown in FIG. 3 indicated that the peak efficiencies were not impacted by the applied voltage unlike the device used in Example 1. Further the peak asymmetry was also consistent across various applied voltages. A summary of the results are presented in Tables 3 and 4 below.

TABLE 3

Effect of applied voltage on peak efficiency using the device of the present invention

| Applied Voltage | $F^-$ | $Cl^-$ | $SO_4^{2-}$ | $NO_3^-$ | $PO_4^{3-}$ |
|---|---|---|---|---|---|
| 4.0 V | 9285 | 13161 | 9026 | 10051 | 5329 |
| 4.5 V | 9306 | 13269 | 9008 | 9971 | 5293 |
| 5.0 V | 9264 | 13371 | 9044 | 10021 | 5307 |

TABLE 4

Effect of applied voltage on peak asymmetry using the device of the present invention

| Applied voltage | $F^-$ | $Cl^-$ | $SO_4^{2-}$ | $NO_3^-$ | $PO_4^{3-}$ |
|---|---|---|---|---|---|
| 4.0 V | 1.47 | 1.31 | 1.26 | 1.43 | 1.69 |
| 4.5 V | 1.40 | 1.28 | 1.28 | 1.43 | 1.68 |
| 5.0 V | 1.42 | 1.27 | 1.28 | 1.42 | 1.69 |

The peak asymmetry also was significantly better with the device of the present invention than the prior art devices. These results are possible with the current device due to the presence of conductive pathways at the outlet of the device. Current efficiency however is maintained due to the weakly dissociated regions in the current design.

EXAMPLE 3 (ANION ANALYSIS)

Figure 4:
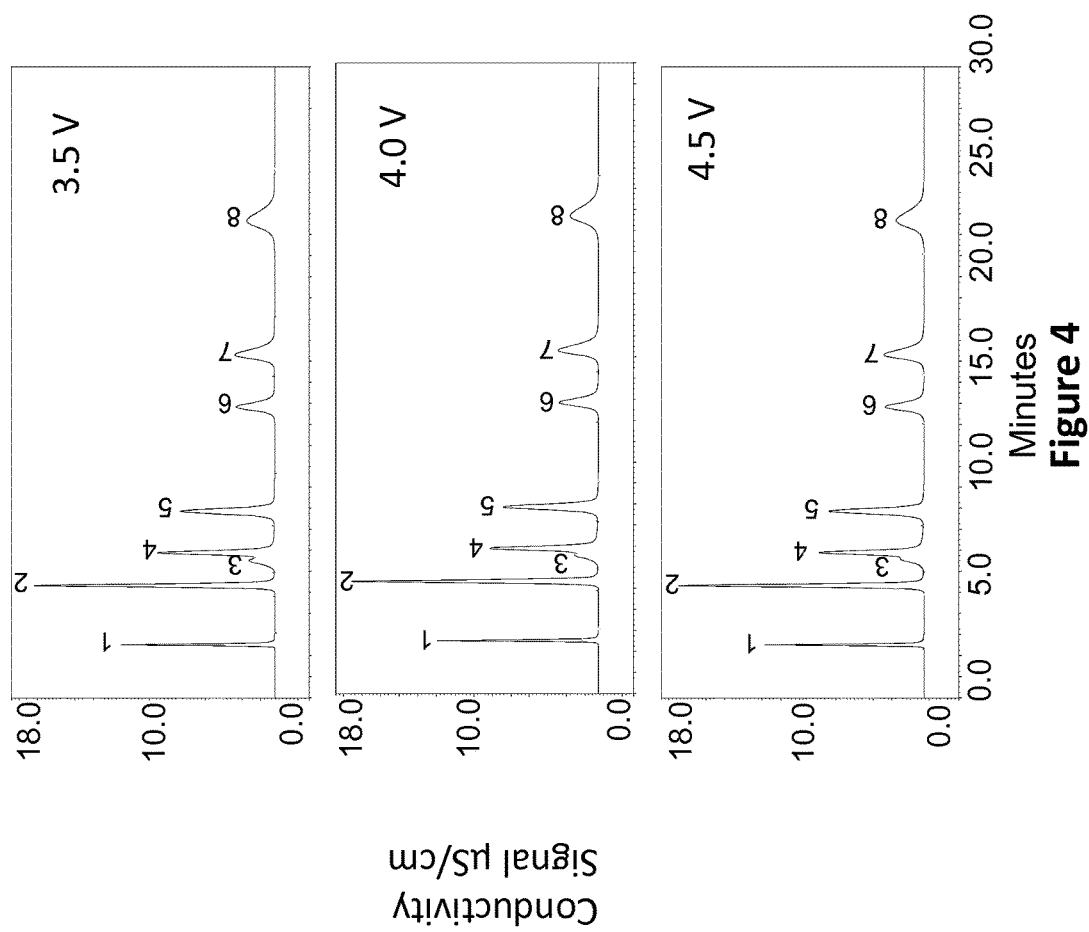
FIG. 4 is a chromatogram illustrating the present invention.

A 4 mm Thermo Scientific™ AERS suppressor (sold by Thermo Fisher Scientific) was packed with a composition comprising of 80% strong sulfonated resin and 20% weak carboxylated resin. The device of Example 2 was tested as a suppressor using an IonPac™ AS15 column 4×250 mm and with an eluent comprising of 38 mM KOH at a flow rate of 1.2 mL/min The injection loop was 25 µL. A sample comprising of seven anion standards with fluoride at 2 mg/L (peak 1), chloride at 10 mg/L (peak 2), carbonate (not quantitated, peak 3), nitrite at 10 mg/L I (peak 4), sulfate at 10 mg/L (peak 5), bromide at 10 mg/L (peak 6), nitrate at 10 mg/L (peak 7) and phosphate at 20 mg/L (peak 8) were evaluated in this study. A constant voltage of 3.5 V, 4.0 V and 4.5 V was used in this study. FIG. 4 shows 3 chromatograms that illustrate the separations at the three different voltages. The peak asymmetry and peak efficiency variations were minimal in the above settings. A summary of the results are presented in the Tables 5 and 6 below.

TABLE 5

Effect of applied voltage on peak efficiency

| Applied Voltage | $F^-$ | $Cl^-$ | $NO_2^-$ | $SO_4^{2-}$ | $Br^-$ | $NO_3^-$ | $PO_4^{3-}$ |
|---|---|---|---|---|---|---|---|
| 3.5 | 4986 | 6432 | n.a. | 5060 | 6128 | 5487 | 3792 |
| 4 | 5489 | 6659 | n.a. | 5058 | 6184 | 5503 | 3826 |
| 4.5 | 5505 | 6677 | n.a. | 5114 | 6175 | 5534 | 3787 |

A relatively smaller variation in peak efficiency was inferred for fluoride based on a 10% variation. The chloride efficiency was changed by 4%. These change values are significantly smaller than what was observed for the device of the prior art which typically showed efficiency losses of greater than 20%. Further operation near the current efficiency level is needed for the prior art devices in order to obtain the best peak shape and peak efficiency performance. These constraints are absent in the present invention due to the greater flexibility of the present design.

TABLE 6

Effect of applied voltage on peak asymmetry

| Applied Voltage (V) | $F^-$ | $Cl^-$ | $NO_2^-$ | $SO_4^{2-}$ | $Br^-$ | $NO_3^-$ | $PO_4^{3-}$ |
|---|---|---|---|---|---|---|---|
| 3.5 | 1.17 | 1.06 | n.a. | 1 | 1.15 | 1.27 | 1.16 |
| 4 | 1.09 | 1.03 | n.a. | 0.99 | 1.14 | 1.28 | 1.18 |
| 4.5 | 1.13 | 1.05 | n.a. | 0.98 | 1.14 | 1.25 | 1.14 |

The peak asymmetry numbers showed a relatively small change over the applied voltage range indicating excellent performance of the suppressor device of the present invention. These results further demonstrate the utility of the resin composition of the present invention.

EXAMPLE 4 (ANION ANALYSIS)

Figure 5:
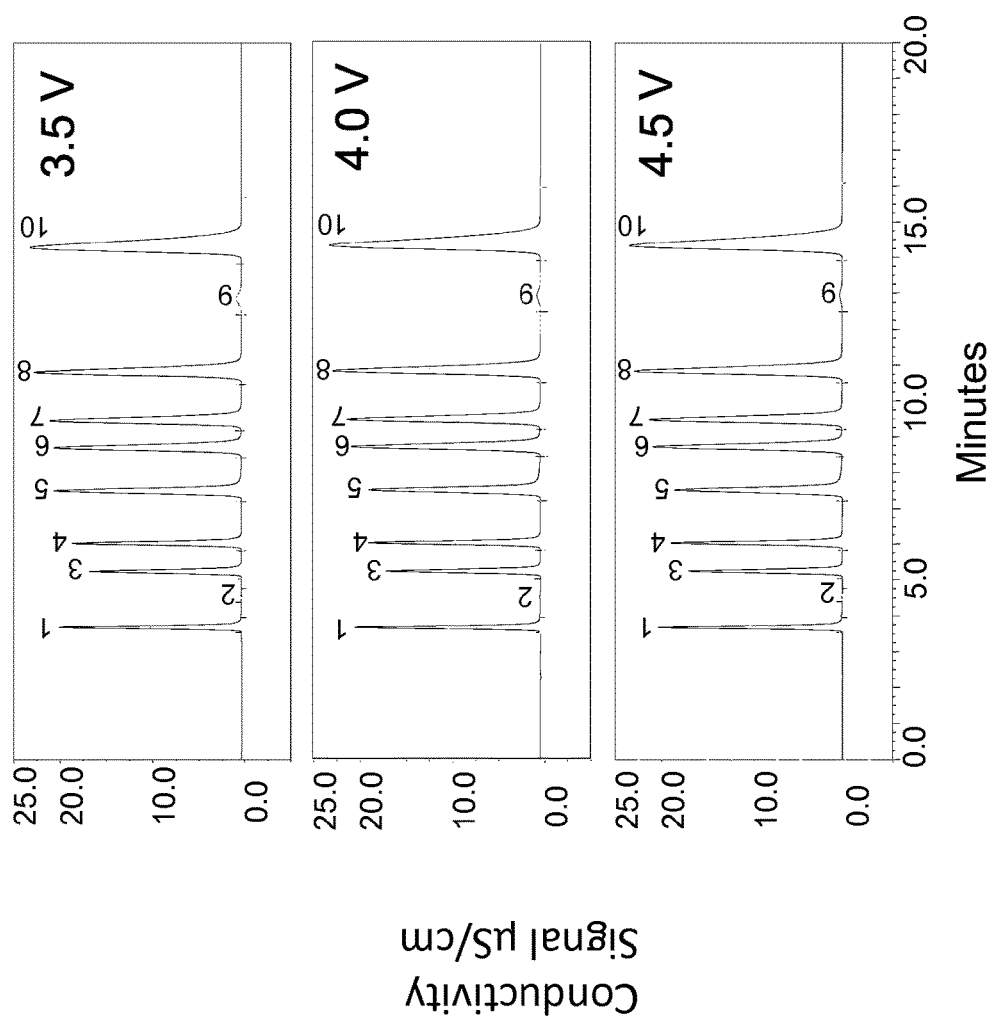
FIG. 5 is a chromatogram illustrating the present invention.

The Thermo Scientific™ AERS suppressor from Example 3 was also evaluated with a 4 mm IonPac™ AS19 chemistry (4×250 mm) using a 20 mM KOH eluent at 1 ml/min flow rate. An injection loop of 25 µL was used in this work. A sample comprising of anion standards comprising of fluoride (peak 1, 3 mg/L), chlorite (peak 2, not quantified), bromate (peak 3, 20 mg/L), chloride (peak 4, 6 mg/L), nitrite (peak 5, 15 mg/L), chlorate (peak 6, 25 mg/L), bromide (peak 7, 25 mg/L, nitrate (peak 8, 25 carbonate (peak 9, not quantified) and sulfate (peak 10, 30 trig/L) was used in this work. The testing was pursued at three applied voltage settings of 3.5 V, 4.0 V and 4.5 V. Comparable separations were established independent of voltage suggesting good performance of the device of the present invention as shown in FIG. 5. The typical peak to peak noise performance of the device was well below 1 nS/cm.

EXAMPLE 5 (ANION ANALYSIS USING A CAPILLARY SUPPRESSOR)

Figure 6:
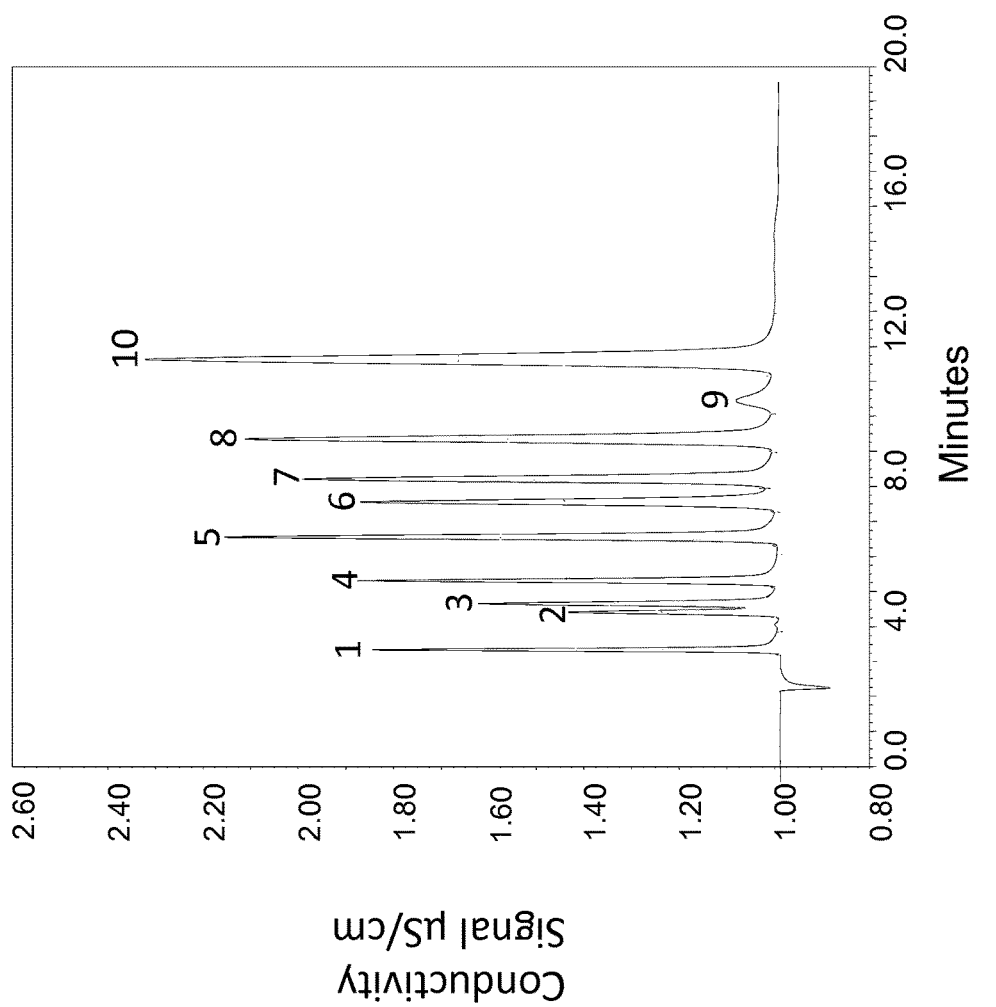
FIG. 6 is a chromatogram illustrating the present invention.

The compositions of the device of the present invention can also be used to improve the current efficiency of prior art suppressor devices. In this example a capillary suppressor (Thermo Scientific™ 0.4 mm ACES suppressor as described in U.S. Pat. Nos. 8,415,168 and 8,216,515) is filled with a composition comprising of 90% strong acid cation exchange resin and 10% weak acid cation exchange resin. The combination was tested using a capillary ion chromatography system using an IonPac AS19 (0.4×250 mm) chemistry. An eluent concentration of 20 mM KOH was used for the analysis. The suppressor was tested using a constant voltage of 4 V. The current efficiency of the device under the test conditions was 75% as opposed to a prior art suppressor that had 100% strong acid resin and operated at a current efficiency of 6%. This improvement of current efficiency would result in lower wattage and possibly improved device life time. The device was tested using a sample mixture comprising of fluoride (peak 1, 0.75 mg/L), chlorite (peak 2, 2.5 mg/L), bromate (peak 3, 5 mg/L), chloride (peak 4, 1.5 mg/L), nitrite (peak 5, 3.75 mg/L), chlorate (peak 6, 6.25 mg/L), bromide (peak 7, 6.25 mg/L), nitrate (peak 8, 6.25 mg/L), carbonate (peak 9, not quantified) and sulfate (peak 10, 7.5 mg/L. Excellent suppression was established with good peak shapes using the device of the present invention as shown in FIG. 6.

EXAMPLE 6 (CATION ANALYSIS)

Figure 7:
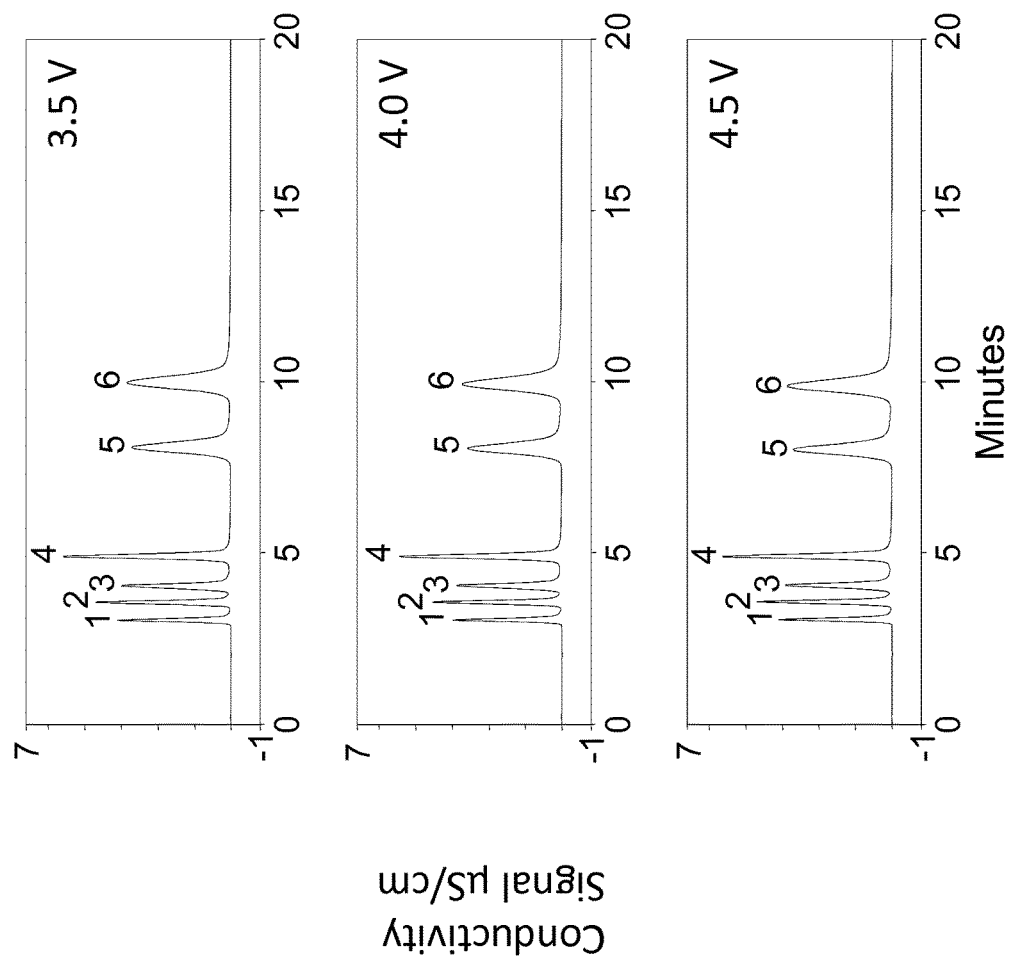
FIG. 7 is a chromatogram illustrating the present invention.
Figure 8:
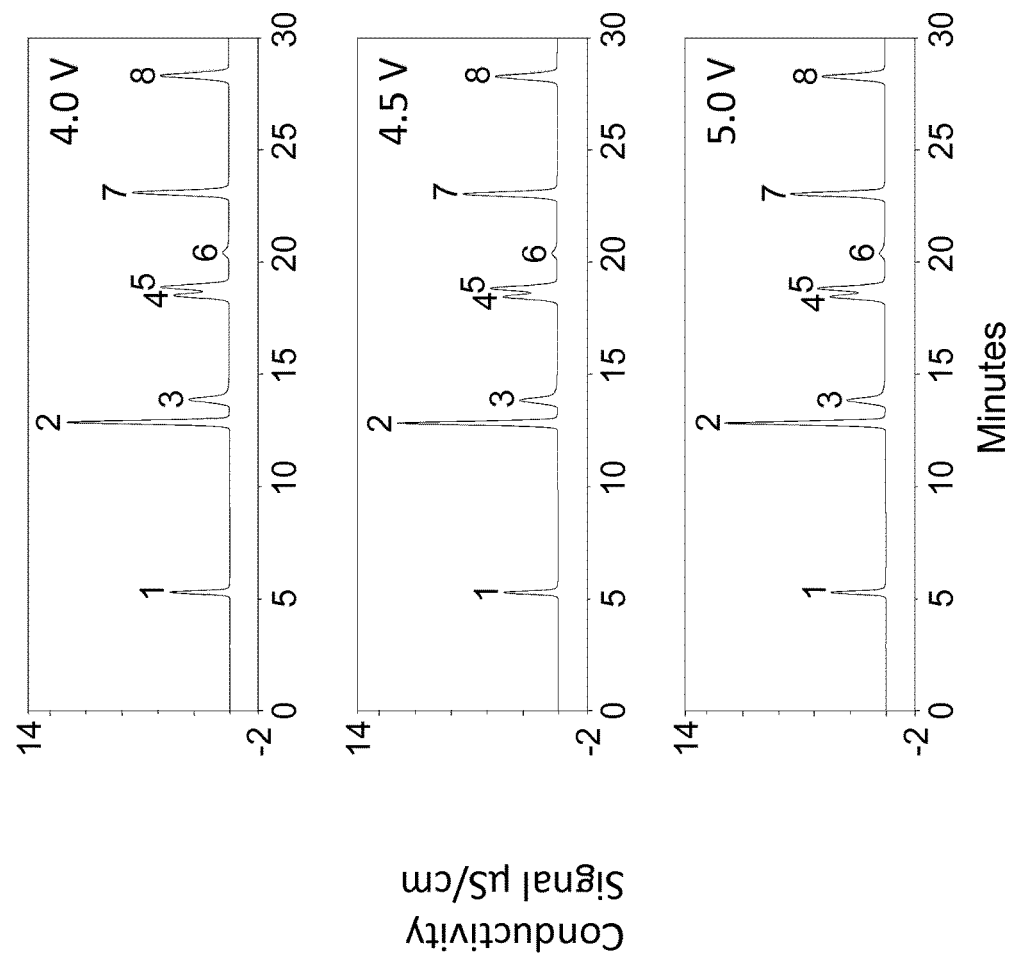
FIG. 8 is a chromatogram illustrating the present invention.

A Thermo Scientific™ CERS 2 mm suppressor according to the present invention was also assembled (available from Thermo Fisher Scientific) as described in the U.S. Pre-Grant Publication 2014/0134050A1. The eluent channel of the device was packed with anion exchange resin with a composition comprising of 90% by weight of a 8% crosslinked quaternary ammonium based strong anion exchange resin and 10% of a tertiary amine based weak base anion exchange resin. The device was tested using an IonPac™CS12A column 2×250 mm and 20 mM methanesulfonic acid eluent. The flow rate was 0.25 mL/min and the injection loop was 5 µL. The CERS 2 mm suppressor was tested at various applied constant voltages to determine the effect of voltage on performance. A sample comprising of a mixture of cation standards was used for this study. The sample consisted of lithium (peak 1, 0.5 mg/L), sodium (peak 2, 2 mg/L), ammonium (peak 3, 2.5 mg/L), potassium (peak 4, 5 mg/L), magnesium (peak 5, 2.5 mg/L) and calcium (peak 6, 5 mg/L). The results as shown in FIG. 7 indicated that peak efficiency was not impacted by the applied voltage unlike the devices of the prior art. Excellent separation and peak shapes were observed for all cations at the three voltage settings used in this testing.

Further the peak asymmetry was also consistent across various voltages suggesting no shape change with applied voltage. A summary of the results are presented in Tables 7 and 8 below.

TABLE 7

Effect of applied voltage on peak efficiency

| Applied Voltage | $Li^+$ | $Na^+$ | $NH_4^+$ | $K^+$ | $Mg^{2+}$ | $Ca^{2+}$ |
|---|---|---|---|---|---|---|
| 3.5 V | 4810 | 5488 | 3848 | 6237 | 3061 | 3209 |
| 4.0 V | 4775 | 5466 | 3786 | 6237 | 3071 | 3221 |
| 4.5 V | 4833 | 5514 | 3779 | 6261 | 3088 | 3241 |

TABLE 8

Effect of applied voltage on peak asymmetry

| Applied Voltage | $Li^+$ | $Na^+$ | $NH_4^+$ | $K^+$ | $Mg^{2+}$ | $Ca^{2+}$ |
|---|---|---|---|---|---|---|
| 3.5 V | 1.1 | 1.1 | 1.05 | 1.13 | 1.16 | 1.19 |
| 4.0 V | 1.15 | 1.13 | 1.08 | 1.13 | 1.21 | 1.25 |
| 4.5 V | 1.15 | 1.14 | 1.09 | 1.12 | 1.22 | 1.25 |

EXAMPLE 7 (ANION ANALYSIS)

The AERS suppressor from Example 2 was also used for testing an eluent containing solvents. The device was tested using a system setup with an IonPac™ AS11-HC 2×250 mm column.

A gradient was used in this work as listed below along with 20% methanol (v/v) as the solvent.

| Gradient Time | Concentration (mM KOH) |
|---|---|
| 0 | 5 |
| 5 | 5 |
| 25 | 50 |
| 30 | 50 |

A mixture comprising of standard anions such as fluoride (peak 1, 2 mg/L), chloride (peak 2, 10 mg/L), nitrite (peak 3, 10 mg/L), bromide (peak 4, 10 mg/L), nitrate (peak 5, 10 mg/L), carbonate (peak 6, not determined), sulfate (peak 7, 10 mg/L) and phosphate (peak 8, 20 mg/L) was analyzed. The effect of applied voltage on the displayed peak efficiency was studied. Excellent performance can be inferred from both the chromatogram shown in FIG. 8 and the peak efficiency numbers plotted at the various voltages suggesting once again that the device was insensitive to the applied voltage. Table 9 shows the results.

TABLE 9

Effect of applied voltage on peak efficiency

| Applied voltage | $F^-$ | $Cl^-$ | $NO_2^-$ | $SO_4^{2-}$ | $Br^-$ | $NO_3^-$ | $PO_4^{3-}$ |
|---|---|---|---|---|---|---|---|
| 4.0 | 5796 | 25721 | 14995 | 24950 | 27156 | 23059 | 52853 |
| 4.5 | 5779 | 25847 | 14786 | 25030 | 27412 | 21553 | 53162 |
| 5.0 | 5723 | 25540 | 14739 | 24652 | 27122 | 19629 | 52913 |

EXAMPLE 8 (ANION ANALYSIS)

The device of Example 6 was also tested using an eluent comprising of borate. The column used in this work was an IonPac™ AS22 2×250 mm column. 200 mM boric acid was pumped into an eluent generator cartridge and a potassium hydroxide gradient was used in this work. The gradient conditions are listed below.

| Gradient Time | Concentration (mM) |
|---|---|
| 0 | 15 |
| 10 | 15 |
| 20 | 85 |
| 30 | 85 |

Figure 9:
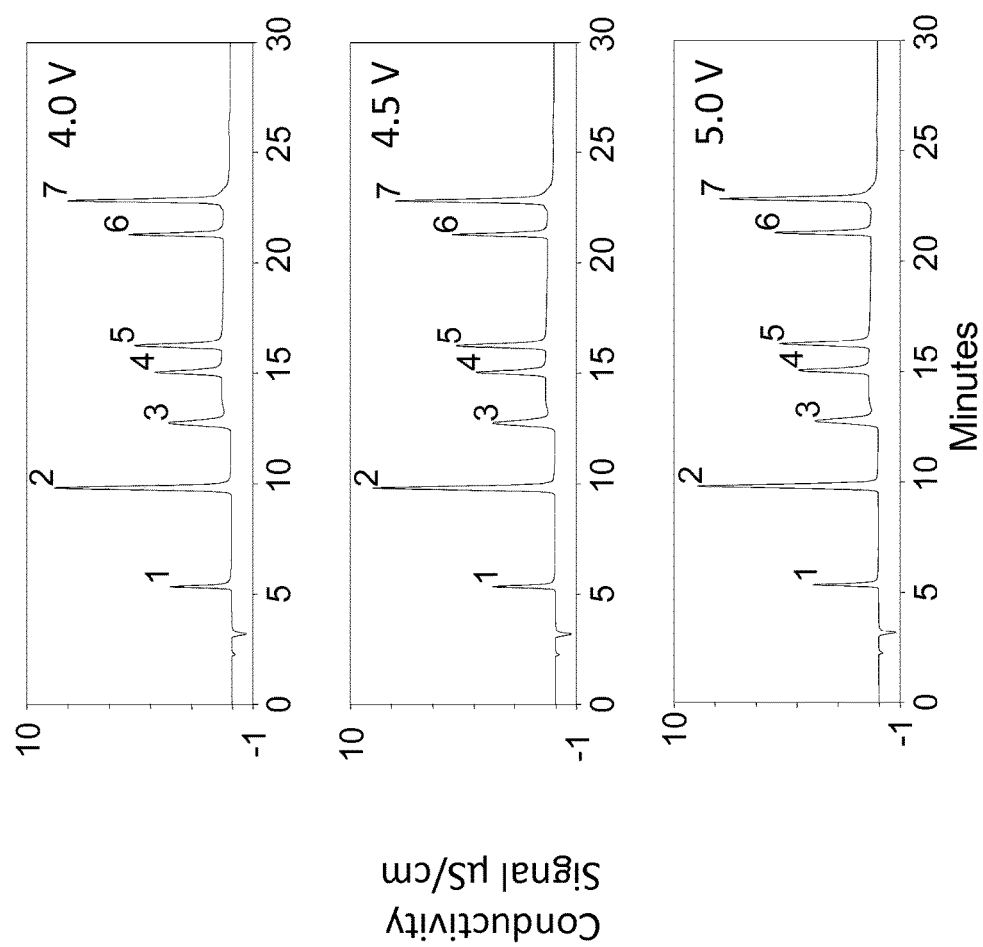
FIG. 9 is a chromatogram illustrating the present invention.

A standard mixture of seven anions included fluoride (peak 1, 2 mg/L), chloride (peak 2, 10 mg/L), nitrite (peak 3, 10 mg/L), bromide (peak 4, 10 mg/L), nitrate (peak 5, 10 mg/L), phosphate (peak 6, 20 mg/L) and sulfate (peak 7, 10 mg/L) was analyzed. The effect of applied voltage on the displayed peak efficiency was studied. Excellent performance can be inferred from both the chromatogram shown in FIG. 9 and the peak efficiency numbers plotted at the various voltages suggesting once again that the device was insensitive to the applied voltage. Table 10 shows the results.

TABLE 10

Effect of applied voltage on peak efficiency

| Applied voltage | $F^-$ | $Cl^-$ | $NO_2^-$ | $Br^-$ | $NO_3^-$ | $PO_4^{3-}$ | $SO_4^{2-}$ |
|---|---|---|---|---|---|---|---|
| 4.0 | 11547 | 15498 | 13170 | 33673 | 38819 | 108754 | 108838 |
| 4.5 | 10693 | 15730 | 13011 | 35725 | 39806 | 105653 | 105086 |
| 5.0 | 10918 | 15159 | 13326 | 34321 | 38670 | 104745 | 101011 |

EXAMPLE 9 (ANION ANALYSIS)

Figure 10:
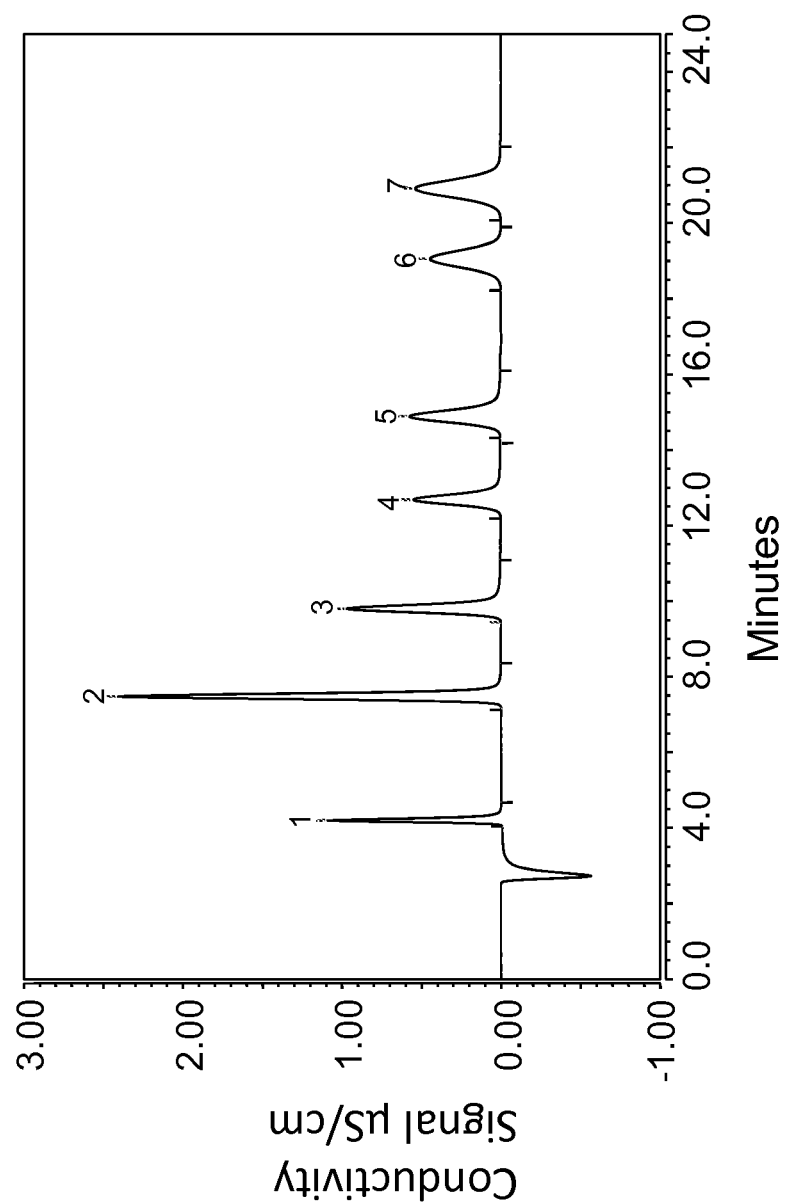
FIG. 10 is a chromatogram illustrating the present invention.
Figure 11:
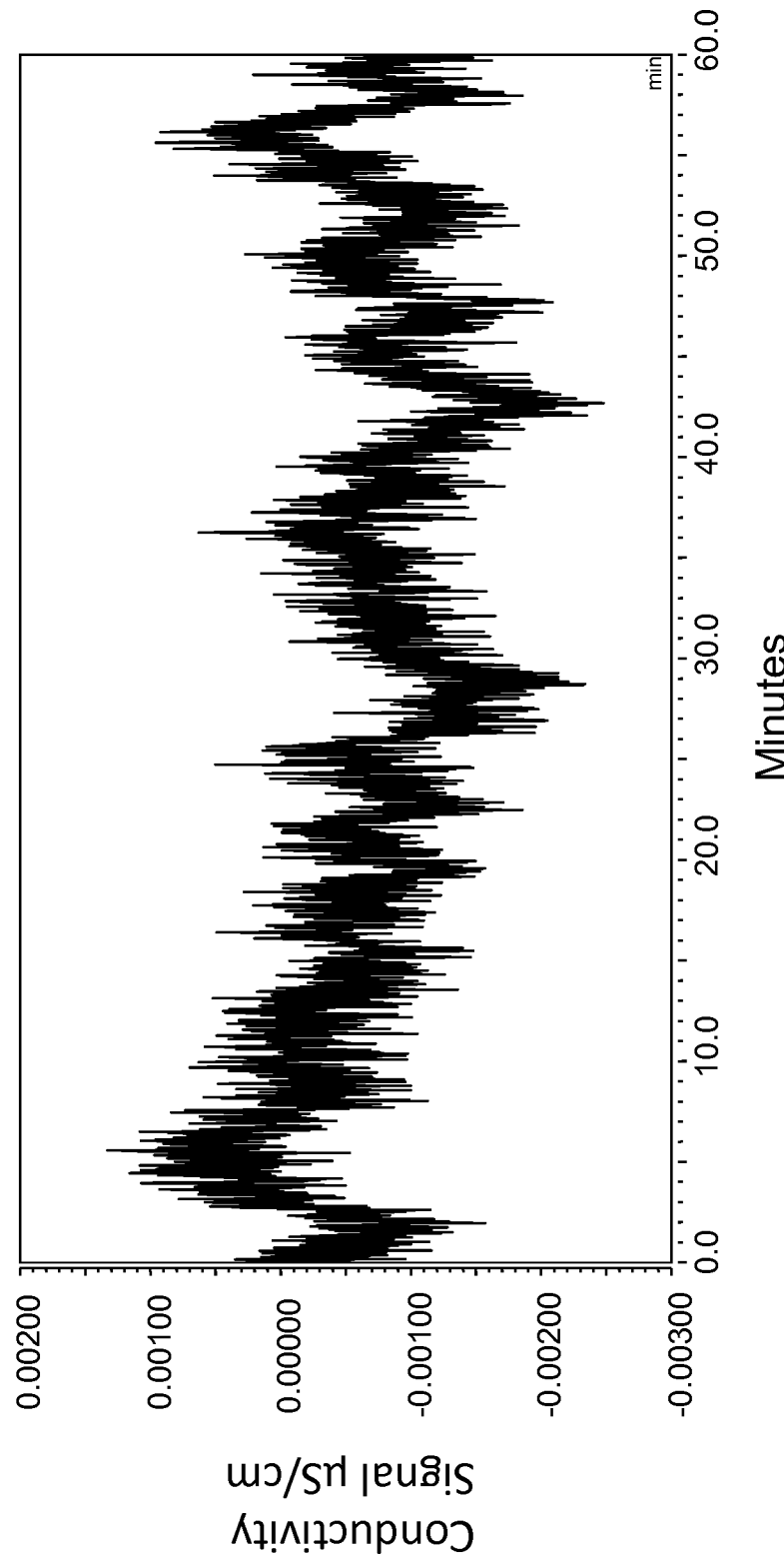
FIG. 11 is a chromatogram illustrating the present invention.

A 4 mm AERS suppressor of the present invention from example 3 was used in this work. The suppressor was tested with an IonPac™ AS23 4×250 mm column at a flow rate of 1 mL/min using an eluent comprising of 4.5 mM sodium carbonate and 0.8 mM sodium bicarbonate eluent. The device was operated at a constant voltage of 4 V. A standard mixture of seven anions (same as example 8) was analyzed using this setup. Excellent peak shapes were observed as shown in FIG. 10 with a chloride efficiency of 11878 plates. The peak to peak noise was also collected for 60 minutes and is shown in FIG. 11. The average noise was in the 1.67 nS/cm regime. A standard suppressor of the prior art showed a typical noise of up to 5 nS/cm for these conditions (data not shown). Thus the device of the present invention is capable of producing low noise performance with carbonate and/or bicarbonate eluents.

What is claimed is:

1. Apparatus for treating an aqueous sample stream including analyte ions of one charge, positive or negative, said apparatus comprising
a first ion exchange barrier capable of passing only ions of opposite charge to said analyte ions;
a sample stream flow channel;
an ion receiving stream flow channel adjacent to said sample stream flow channel and separated therefrom by said first ion exchange barrier;
a stationary flow-through first ion exchange packing disposed in said sample stream flow channel of the same charge, positive or negative, as said first ion exchange barrier;
said stationary flow-through first ion exchange packing having exchangeable ions of opposite charge to said analyte ions and comprising pre-mixed ion exchange particles, said pre-mixed ion exchange particles comprising, in an intimate mixture, a first ion exchange portion with strong ionizable groups and a second ion exchange portion with weak ionizable groups, both portions having ion exchange capacity of the same charge, positive or negative; and
first and second electrodes in electrical communication with said sample stream flow channel and said ion receiving stream flow channel, respectively.

2. The apparatus of claim 1 further comprising second stationary flow-through ion exchange packing disposed in said ion receiving stream flow channel of the same charge, positive or negative, as said first ion exchange barrier.

3. The apparatus of claim 1 wherein said first ion exchange portion ranges from about 40 to 97 weight % of said pre-mixed ion exchange particles.

4. The apparatus of claim 3 wherein said second ion exchange portion ranges from about 3 to 60 weight % of said pre-mixed ion exchange particles.

5. The apparatus of claim 1 in combination with apparatus for performing ion chromatography, further comprising a chromatographic separator in fluid combination with said sample stream flow channel; and a detector for said analyte ions in fluid communication with an outlet of said sample stream flow channel.

6. The apparatus of claim 1 for pretreatment of a sample stream and in combination with chromatography apparatus, said apparatus further comprising a chromatographic separator having an inlet and an outlet, said chromatographic separator inlet being in fluid communication with said sample stream flow channel; and a detector for said analyte in fluid communication with the outlet of said chromatographic separator.

7. The apparatus of claim 1 further comprising a second ion exchange barrier on the opposite side of said sample stream flow channel from said first ion exchange barrier and of the same charge, positive or negative; and an ion source stream flow channel adjacent said second ion exchange barrier.

8. The apparatus of claim 7 in which said second electrode is disposed in said ion receiving flow stream channel and said first electrode is disposed in said ion source stream flow channel.

9. The apparatus of claim 1 wherein said first electrode is disposed in said ion receiving stream flow channel and said second electrode is disposed in said sample stream flow channel.

10. The apparatus of claim 1 further comprising a constant voltage source connected to said first and second electrodes.

11. A method for treating an aqueous sample stream including analyte ions of one charge, positive or negative, said method comprising
flowing the sample stream through a sample stream flow channel and out an outlet thereof in a device; and
simultaneously flowing an aqueous ion receiving stream through an ion receiving stream flow channel in said device, said ion receiving stream flow channel separated from said sample stream flow channel by a first ion exchange barrier capable of passing only ions of opposite charge to said analyte ions, while passing a current between said sample stream flow channel and said ion receiving stream flow channel;
said sample stream flow channel having stationary flow-through first ion exchange packing having exchangeable ions, said exchangeable ions having an opposite charge to said analyte ions disposed in said sample stream flow channel where both said stationary flow-through first ion exchange packing and said analyte ions have the same charge, positive or negative, as said first ion exchange barrier;
said stationary flow-through first ion exchange packing comprising pre-mixed ion exchange particles, said pre-mixed ion exchange particles comprising, in an intimate mixture, a first ion exchange portion with strong ionizable groups and a second ion exchange portion with weak ionizable groups, both portions having the same charge, positive or negative.

12. The method of claim 11 in which said ion receiving stream flow channel includes stationary flow-through second ion exchange packing of the same charge as said first ion exchange barrier, positive or negative.

13. The method of claim 11 wherein said first ion exchange portion ranges from about 40 to 97 weight % of said pre-mixed ion exchange particles.

14. The method of claim 13 wherein said second ion exchange portion ranges from about 3 to 60 weight % of said pre-mixed ion exchange particles.

15. The method of claim 11 in which said passed current is generated at a substantially constant voltage during said treating method.

16. The method of claim 11 further comprising flowing matrix ions, of opposite charge to said analyte ions, to said sample stream flow channel; and transporting the matrix ions out of said sample stream flow channel across said first ion exchange barrier.

17. The method of claim 16 further comprising detecting said analyte ions flowing out the outlet of said sample stream flow channel.

18. The method of claim 11 further comprising flowing an ion source aqueous stream through an aqueous stream ion source stream flow channel in said device separated from said sample stream flow channel by a second ion exchange barrier capable of passing only ions of opposite charge to said analyte ions, said current passing from said ion source stream flow channel through said sample stream flow channel to said ion receiving stream flow channel.

19. The method of claim 18 wherein said current is passed between a first electrode disposed in said ion receiving flow channel and a second electrode disposed in said ion source stream flow channel.

\* \* \* \* \*

UNITED STATES PATENT AND TRADEMARK OFFICE
CERTIFICATE OF CORRECTION

PATENT NO. : 10,175,211 B2  
APPLICATION NO. : 14/587780  
DATED : January 8, 2019  
INVENTOR(S) : Kannan Srinivasan et al.

Page 1 of 1

It is certified that error appears in the above-identified patent and that said Letters Patent is hereby corrected as shown below:

On the Title Page

Item [57], Column 2, Line 6: replace "bather." with -- barrier. --

Item [57], Column 2, Line 8: replace "bather." with -- barrier. --

Signed and Sealed this  
Seventeenth Day of August, 2021

Drew Hirshfeld  
*Performing the Functions and Duties of the*  
*Under Secretary of Commerce for Intellectual Property and*  
*Director of the United States Patent and Trademark Office*